(12) United States Patent
Jones (10) Patent No.: US 7,927,661 B2
(45) Date of Patent: Apr. 19, 2011

(54) METHODS OF DEPOSITING A METAL OXIDE LAYER OR FILM USING A RARE EARTH METAL PRECURSOR

(75) Inventor: Anthony Copeland Jones, Eccleston Park (GB)

(73) Assignee: Sigma-Aldrich Co., St. Louis, MO (US)

( * ) Notice: Subject to any disclaimer, the term of this patent is extended or adjusted under 35 U.S.C. 154(b) by 1259 days.

(21) Appl. No.: 10/548,946

(22) PCT Filed: Mar. 11, 2004

(86) PCT No.: PCT/GB2004/001047
§ 371 (c)(1), (2), (4) Date: Aug. 29, 2006

(87) PCT Pub. No.: WO2004/083479
PCT Pub. Date: Sep. 30, 2004

(65) Prior Publication Data
US 2007/0190684 A1    Aug. 16, 2007

(30) Foreign Application Priority Data

Mar. 17, 2003  (GB) .................................. 0306027.4
Sep. 12, 2003  (GB) .................................. 0321409.5
Nov. 1, 2003   (GB) .................................. 0325752.4

(51) Int. Cl.
C23C 16/40 (2006.01)
(52) U.S. Cl. ............ 427/255.31; 427/255.32; 427/255.6
(58) Field of Classification Search ............. 427/255.29, 427/255.31, 255.6, 255.32; 117/88, 104
See application file for complete search history.

(56) References Cited

U.S. PATENT DOCUMENTS

| 5,625,587 | A | * | 4/1997 | Peng et al. | 365/145 |
|---|---|---|---|---|---|
| 5,866,204 | A | * | 2/1999 | Robbie et al. | 427/256 |
| 6,080,283 | A |   | 6/2000 | Ray | 204/164 |
| 6,430,458 | B1 |   | 8/2002 | Mosely | 700/121 |
| 6,852,167 | B2 | * | 2/2005 | Ahn | 118/715 |
| 7,736,446 | B2 | * | 6/2010 | Takashima et al. | 148/284 |
| 2002/0172768 | A1 | * | 11/2002 | Endo et al. | 427/255.28 |
| 2003/0072882 | A1 | * | 4/2003 | Niinisto et al. | 427/255.28 |

(Continued)

FOREIGN PATENT DOCUMENTS

EP    0 563 557 A3    2/1993

(Continued)

OTHER PUBLICATIONS

Wright, P.J., et al., "Metal organic chemical vapor deposition (MOCVD) of oxides and ferroelectric materials." Journal of Materials Science: Materials in Electronics 13 (2002), pp. 671-678.*

(Continued)

*Primary Examiner* — Bret Chen
(74) *Attorney, Agent, or Firm* — Harness, Dickey & Pierce, P.L.C.

(57) ABSTRACT

Methods of depositing a single or mixed metal oxide layer or film are described herein. The methods use a rare earth metal precursor are described herein. The rare earth metal precursors have a general formula $M[OCR^1(R^2)(CH_2)X]_3$, wherein M is a rare earth metal, $R^1$ is H or an alkyl group, $R^2$ is an optionally substituted alkyl group and X is selected from OR and NR, wherein R is an alkyl group or a substituted alkyl group.

21 Claims, 7 Drawing Sheets

X-ray crystal structure of [LiPr(mmp)₃Cl]₂

U.S. PATENT DOCUMENTS

2006/0141155 A1\* 6/2006 Gordon et al. .......... 427/255.19

FOREIGN PATENT DOCUMENTS

| JP | 07285969 A | 10/1995 |
| JP | 07-315847 | 12/1995 |
| JP | 08-217461 | 8/1996 |
| JP | 2002363122 A | 12/2002 |
| TW | 446754 | 7/2001 |
| TW | 518368 | 1/2003 |
| WO | WO 02/20864 | 3/2002 |
| WO | WO 03/004721 A1 | 1/2003 |
| WO | WO 03/035926 A3 | 5/2003 |
| WO | WO 2009/143456 | 11/2009 |
| WO | WO 2009/143460 | 11/2009 |

OTHER PUBLICATIONS

Jones, Anthony C., et al., "Some recent developments in the MOCVD and ALD of high-k dielectric oxides". Journal of Materials Chemistry, Sep. 2004, pp. 1-12.\*

Aspinall, Helen C., "Growth of Praseodymium Oxide Thin Films by Liquid Injection of MOCVD using a Novel Praseodymium Alkoxide Precursor". Chemical Vapor Deposition 2003, 9, No. 5, 2003, pp. 235-238.\*

Song, H. et al., Synthesis and Characterization of Volatile Metal β-diketonate chelates of M(DPM)$n$ (M=Ce, Gd, Y, Zr, $n$=3,4) Used as Precursors of MOCVD, Journal of Crystal Growth, 2003, 250: 423-430.

Malandrino, G. et al., Nanostructured Cerium Dioxide Thin Films by MOCVD: Influence of the Substrate Nature and Processing Parameters, Electrochemical Society Proceedings, Aug. 2003: 1112-1118.

Nigro, R. et al., MOCVD Growth of $Pr_2O_3$ High-K Gate Dielectric for Silicon: Synthesis and Structural Investigation, Electrochemical Society Proceedings, Aug. 2003: 915-922.

PCT International Search Report for Application No. PCT/GB2004/001047 dated Oct. 11, 2004, pp. 1-4.

Anwander, R. et al., Volatile Donor-Functionalized Alkoxy Derivatives of Lutetium and Their Structural Characterization, Inorg. Chem., 1997, 36: 3545-3552.

Great Britain Search Report for Application No. GB0405441.7 dated Jul. 5, 2004.

Herrmann, et al. (1992) "Volatile neodymium and yttrium alkoxides with new bulky chelating ligands" Chemical Reports, 125(11):2399-2405.

Wandass, et al. (1990) "Application of sol-gel techniques to thin-film superconductor systems." AIP Conference Proceedings, 200:157-164.

Herrmann, et al. (1995) "Volatile metal alkoxides according to the concept of donor functionalization." Angewandte Chemie International Edition English, 34:2187-2206.

\* cited by examiner

X-ray crystal structure of [LiPr(mmp)₃Cl]₂

FIG. 1

XRD spectra of Pr-oxide films deposited at 400°C and 600°C from [Pr(mmp)$_3$]. * denotes the dominant (101) reflection of the secondary θ-Pr$_2$O$_3$ phase.

FIG. 2

SEM image of a Pr-oxide film deposited at 400°C from [Pr(mmp)$_3$]

METHODS OF DEPOSITING A METAL OXIDE LAYER OR FILM USING A RARE EARTH METAL PRECURSOR

This invention concerns precursors for deposition of metal oxide layers or films, methods of making such precursors and methods of depositing metal oxide layers or films using such precursors. This invention is particularly, but not exclusively, concerned with precursors for the growth of praseodymium oxide and other lanthanide (rare earth) metal oxides by chemical vapour deposition.

Rare-earth oxides $M_2O_3$ (M=Pr, La, Gd, Nd) are good insulators due to their large band-gaps (eg. 3.9 eV for $Pr_2O_3$, 5.6 eV for $Gd_2O_3$), they have high dielectric constants ($Gd_2O_3$ κ=16, $La_2O_3$ κ=27, $Pr_2O_3$ κ=26-30) and higher thermodynamic stability on silicon than $ZrO_2$ and $HfO_2$, making them very attractive materials for high-κ dielectric applications. Another attractive feature of some rare earth oxides (eg. $Pr_2O_3$, $Gd_2O_3$) is their relatively close lattice match to silicon, offering the possibility of epitaxial growth, eliminating problems related to grain boundaries in polycrystalline films.

Metalorganic chemical vapour deposition (MOCVD) is an attractive technique for the deposition of these materials, offering the potential for large area growth, good composition control and film uniformity, and excellent conformal step coverage at device dimensions less than 2 μm, which is particularly important in microelectronics applications.

An essential requirement for a successful MOCVD process is the availability of precursors with the appropriate physical properties for vapour phase transport and a suitable reactivity for deposition. There must be an adequate temperature window between evaporation and decomposition, and for most electronics applications oxide deposition is restricted to temperatures in the region of 500° C., to prevent degradation of the underlying silicon circuitry and metal interconnects.

$Pr_2O_3$ thin films have previously been deposited by physical vapour deposition techniques such as MBE and pulsed laser deposition. Metalorganic chemical vapour deposition (MOCVD) has a number of potential advantages over these techniques, such as large area growth capability, good composition control, high film densities and excellent conformal step coverage, but there have been very few reports on the MOCVD of Praseodymium oxide, due largely to a lack of suitable precursors.

Recently the MOCVD of a range of praseodymium-oxides ($PrO_2$, $Pr_6O_{11}$, $Pr_2O_3$) has been reported using Pr(thd)$_3$ (thd=2,2,6,6,-tetramethylheptane-3,5-dionate) (R. Lo Nigro, R. G. Toro, G. Malandrino, V. Raineri, I. L. Fragala, Proceedings of EURO CVD 14, Apr. 27-May 2, 2003, Paris France (eds. M. D. Allendorf, F. Maury, F. Teyssandier), Electrochem. Soc. Proc. 2003, 2003-08, 915). However, the deposition temperature used (750° C.) is incompatible with the low deposition temperature generally required for microelectronics applications, where high growth temperatures can lead to problems such as increased dopant diffusion The use of [Pr(thd)$_3$] may also lead to the presence in the Pr-oxide film of residual carbon, a common contaminant in oxide films grown using metal β-diketonates [Pr(hfa)$_3$(diglyme)] Pr(hfa)$_3$ diglyme (hfa=1,1,1,5,5,5-hexafluoro-2,4-pentanedionate, diglyme=$CH_3O(CH_2CH_2O)_2CH_3$) was also investigated by these researchers, but led only to the unwanted oxyfluoride phase, PrOF.

Metal allcoxides have been widely used in the MOCVD of metal oxides, and generally allow lower growth temperatures than the more thermally stable metal β-diketonate precursors. There are no reports in the literature into the use of rare-earth alkoxide precursors in MOCVD. This is because the large ionic radius of the highly positively charged lanthanide(III) ions leads to the formation of bridging intermolecular metal-oxygen bonds, resulting in the majority of the simple alkoxide complexes being polymeric or oligomeric, with a corresponding low volatility which makes them unsuitable for MOCVD applications.

An object of this invention is to provide stable volatile rare earth metal oxide precursors suitable for use in chemical vapour deposition techniques.

It has been surprisingly found that the donor functionalised alkoxy ligand 1-methoxy-2-methyl-2-propanolate [$OCMe_2CH_2OMe$, mmp] is effective in inhibiting oligomerisation in praseodymium alkoxide complexes, as well as increasing the ambient stability of the complexes.

Accordingly the present invention provides rare earth metal precursors for use in MOCVD techniques having a ligand of the general formula $OCR^1(R^2)CH_2X$ wherein $R^1$ is H or an alkyl group, $R^2$ is an optionally substituted alkyl group and X is selected from OR and $NR_2$, wherein R is an alkyl group or a substituted alkyl group.

Preferred precursors according to the invention have the following general formula:

wherein M is a rare earth metal, especially praseodymium, $R^1$ is H or an alkyl group, $R^2$ is an optionally substituted alkyl group and X is selected from OR and $NR^2$, wherein R is an alkyl group or a substituted alkyl group, n=1 to 4.

The preferred ligand of the formula $OCR^1(R^2)(CH_2)_nX$ (n=1) is 1-methoxy-2-methyl-2-propanolate (mmp) [$OCMe_2CH_2OMe$], but other donor functionalised alkoxide ligands may be used. These may include but are not limited to $OCH(Me)CH_2OMe$, $OCEt_2CH_2OMe$, $OCH(Et)CH_2OMe$, $OC(Pr^i)_2CH_2OMe$, $OCH(Pr^i)CH_2OMe$, $OC(Bu^t)_2CH_2OMe$, $OCH(Bu^t)CH_2OMe$, $OCH(Bu^t)CH_2OEt$, $OC(Bu^t)_2CH_2OEt$, $OC(Pr^i)_2CH_2OEt$, $OCH(Bu^t)CH_2NEt_2$, $OC(Pr^i)_2CH_2OC_2H_4OMe$ and $OC(Bu^t)(CH_2OPr^i)_2$.

The invention further provides a first method of making rare earth metal oxide precursors for use in MOCVD techniques comprising reacting $HOCR^1(R^2)(CH_2)_nX$ wherein $R^1$, $R^2$ and X are as defined above, such as mmpH, with the corresponding rare earth metal alkylamide $M(NR_2)_3$ or silylamide precursor $M(N(SiR_3)_2)_3$, especially praseodymium silylamide precursor, $Pr\{N(Sie_3)_2\}_3$, in appropriate molar proportions, wherein R=alkyl, such as, for example, Me, Et and $Pr^i$.

According to the invention an alternative method of general synthesis of lanthanide and rare earth element complexes of the formula $M[OCR^1(R^2)CH_2X]_3$ as defined above, such as, Ln(mmp)$_3$, involves the salt exchange reaction of Ln(NO$_3$)$_3$(tetraglyme) with appropriate molar equivalents of Na($M[OCR^1(R^2)CH_2X]_3$, such as Na(mmp), in tetrahydrofuran solvent. A similar method may be used for the preparation of Sc(mmp)$_3$ and Y(mmp)$_3$.

Precursors according to the invention may be used in depositing single or mixed oxide layers or films by conventional MOCVD, in which the precursor is contained in a metalorganic bubbler, or by liquid injection MOCVD, in which the precursor is dissolved in an appropriate inert organic solvent and then evaporated into the vapour phase using a heated evaporator. Appropriate solvents include aliphatic hydrocarbons, such as hexane, heptane and nonane, aromatic hydrocarbons such as toluene, and aliphatic and cyclic ethers. Additives such as polydentate ethers including diglyme, $CH_3O(CH_2CH_2O)_2CH_3$, triglyme, $CH_3O(CH_2CH_2O)_3CH_3$, tetraglyme, $CH_3O(CH_2CH_2O)_4CH_3$, and donor functionalised alcohols such as 1 methoxy-2-methyl-2-propanol HOCMe$_2$CH$_2$OMe (mmpH) may also be added to the solvent, as these may render the precursors of the invention, especially Ln(mmp)$_3$ (Ln=lanthanide such as La, Pr, Gd, Nd etc.), less reactive to air and moisture and may improve the evaporation characteristics of the precursor solution. The amount of additive added to the solvent will typically be in the region of 3 mol. equiv.: 1 mol. equiv. precursor. Lower amounts of additive are less effective but amounts of more than 3 mol. equiv. may be used.

The precursors may also be suitable for use in the deposition of praseodymium oxide films by other chemical vapour deposition techniques, such as atomic layer deposition (ALD).

The M[OCR$^1$(R$^2$)(CH$_2$)$_n$X]$_3$ precursor may also be suitable for the deposition of rare-earth oxide films using non-vapour phase deposition techniques, such as sol-gel deposition and metal-organic decomposition, where the new complexes may undergo a more controlled hydrolysis reactions than simple M(OR)$_3$ complexes.

Other volatile rare earth precursors for use in MOCVD, ALD or sol-gel processes according to the invention may include lanthanide (rare-earth) elements, such as La, Ce, Gd, Nd, Pm, Sm, Eu, Th, Dy, Ho, Er, Tm, Yb and Lu as well as Group IIIB elements including Sc and Y.

The precursors according to the invention can also be used, in combination with an appropriate silicon precursor for the MOCVD of lanthanide silicates, LnSi$_x$O$_y$, and with appropriate co-precursors for the MOCVD of multi-component oxides, such as Pr$_x$M$_y$O$_z$ containing praseodymium, or other rare earth metals with metals (M) from other groups of the periodic table.

The invention will now be further described by means of the following Examples and with reference to the accompanying drawings, in which.

EXAMPLE 1

Preparation of Pr(mmp)$_3$

MmpH (0.487 cm$^3$, 4.23 mmol) was added to a solution of [Pr{N(SiMe$_3$)$_2$}$_3$] (0.878 g, 1.41 mmol) in toluene (80 cm$^3$). The solution was stirred at room temperature for 10 min and then solvent and HN(SiMe$_3$)$_2$ was removed in vacuo to give a green oil.

Microanalysis: Found. C, 38.0; H, 6.60%. Calculated. For C$_{15}$H$_{33}$O$_6$Pr C, 40.01; H, 7.39%.

IR (ν cm$^{-1}$, neat liquid, NaCl plates): 2960 vs; 1496 m; 1458 s; 1383 m; 1357 s; 1274 s, 1229 vs, 1205 s; 1171 vs; 1113 vs; 1086 vs; 997 vs; 967 vs; 943 vs; 915 m; 828 w; 786 m; 730 s; 695 m.

NMR spectroscopy (CDCl$_3$; 400 MHz): (All resonances are broadened due to the paramagnetic Pr$^{3+}$ (4f$^2$). Integrals of these broad resonances are note reported due to the lack of precision): 100.5, 72.5, 69.7, 67.0, 64.0, 63.7, 62.4, 60.7, 58.4, 57.0, 56.0, 54.0, 53.5, 50.5, 48.2, 47.2, 42.2, 40.7, 19.1, 18.6, 18.0, 17.7, 15.3, 13.9, 12.7, 11.2, 3.1, 1.2, −4.7, −10.5, −11.8, −12.5, −13.0, −15.5, −19.0, −20.5, −24.4, −30.2, −40.1, −43.6, −45.3, −46.2, −54.0

Figure 1:
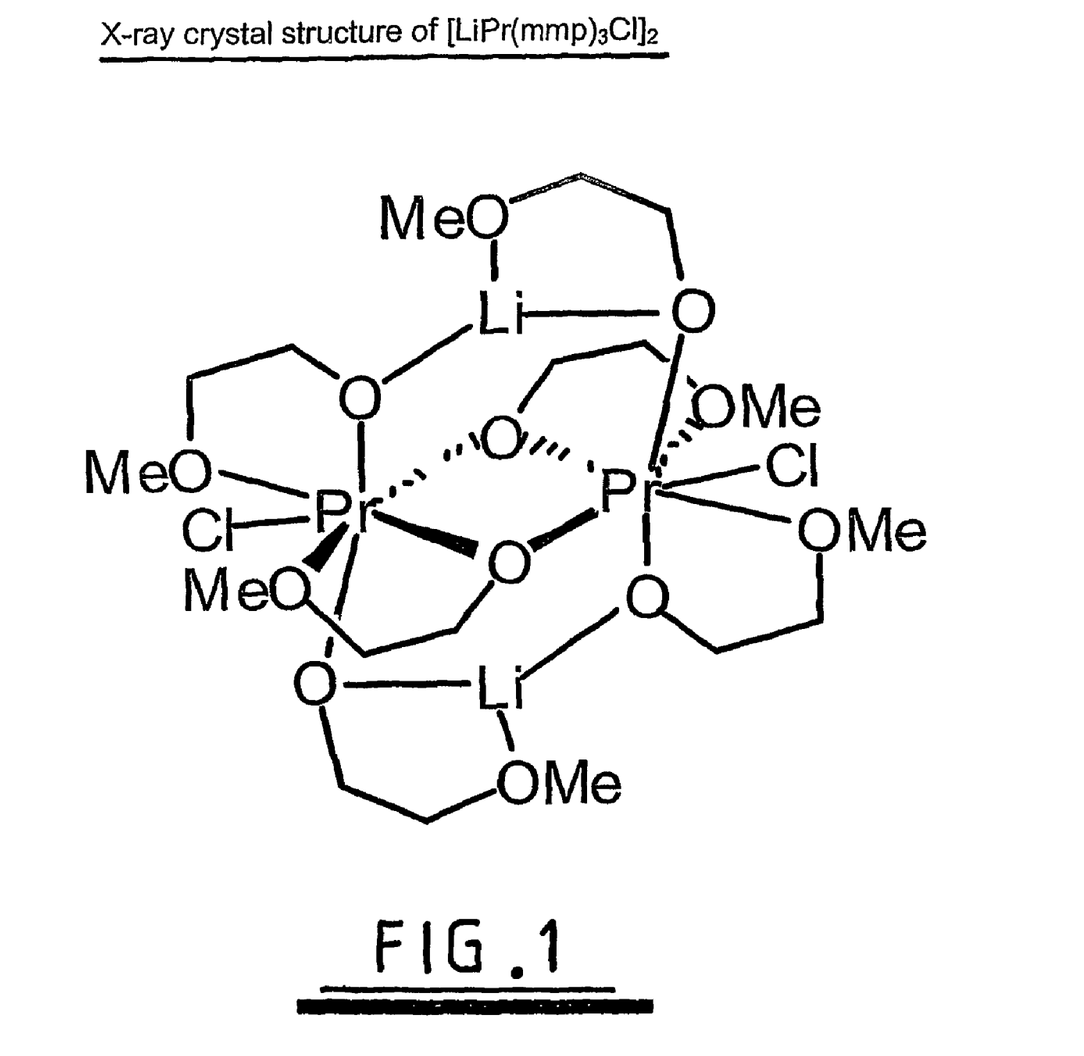
FIG. 1 shows the X-ray crystal structure of [LiPr(mmp)$_3$Cl]$_2$.

The liquid nature of Pr(mmp)$_3$ precludes structural characterisation by single crystal X-ray diffraction, but In the presence of LiCl a crystalline complex with the formula [LiPr(mmp)$_3$Cl]$_2$ was isolated, providing further good evidence that the stoichiometry of the oil was [Pr(mmp)$_3$]. This complex was characterized by single crystal X-ray diffraction and its structure is shown in FIG. 1 of the drawings.

EXAMPLE 2

Pr(mmp)$_3$ was found to be a suitable precursor for the deposition of praseodymium oxide thin films by MOCVD. The praseodymium oxide films were deposited by liquid injection MOCVD using a 0.1M solution of Pr(mmp)$_3$ in toluene (14 cm$^3$) to give a 0.1 M solution. The addition of tetraglyme CH$_3$O(CH$_2$CH$_2$O)$_4$CH$_3$ was found to stabilise the Pr(mmp)$_3$ solution by making it less reactive to air and moisture and improving the transport properties of the precursor. The growth conditions used to deposit Pr-oxide thin films by liquid injection MOCVD using a toluene solution of Pr(mmp)$_3$ are summarised in Table 1.

TABLE 1

| | |
|---|---|
| Reactor pressure | 1 mbar |
| Evaporator temperature | 170° C. |
| Substrate temperature | 350-600° C. |
| Precursor solution concentration | 0.1 M in toluene with 3 mol equiv. of added tetraglyme |
| Precursor solution injection rate | 8 cm$^3$ hr$^{-1}$ |
| Argon flow rate | 400 cm$^3$ min$^{-1}$ |
| Oxygen flow rate | 100 cm$^3$ min$^{-1}$ |
| Substrates | Si(100) |
| Typical oxide growth rates | 0.2 μm hr$^{-1}$ |

Figure 2:
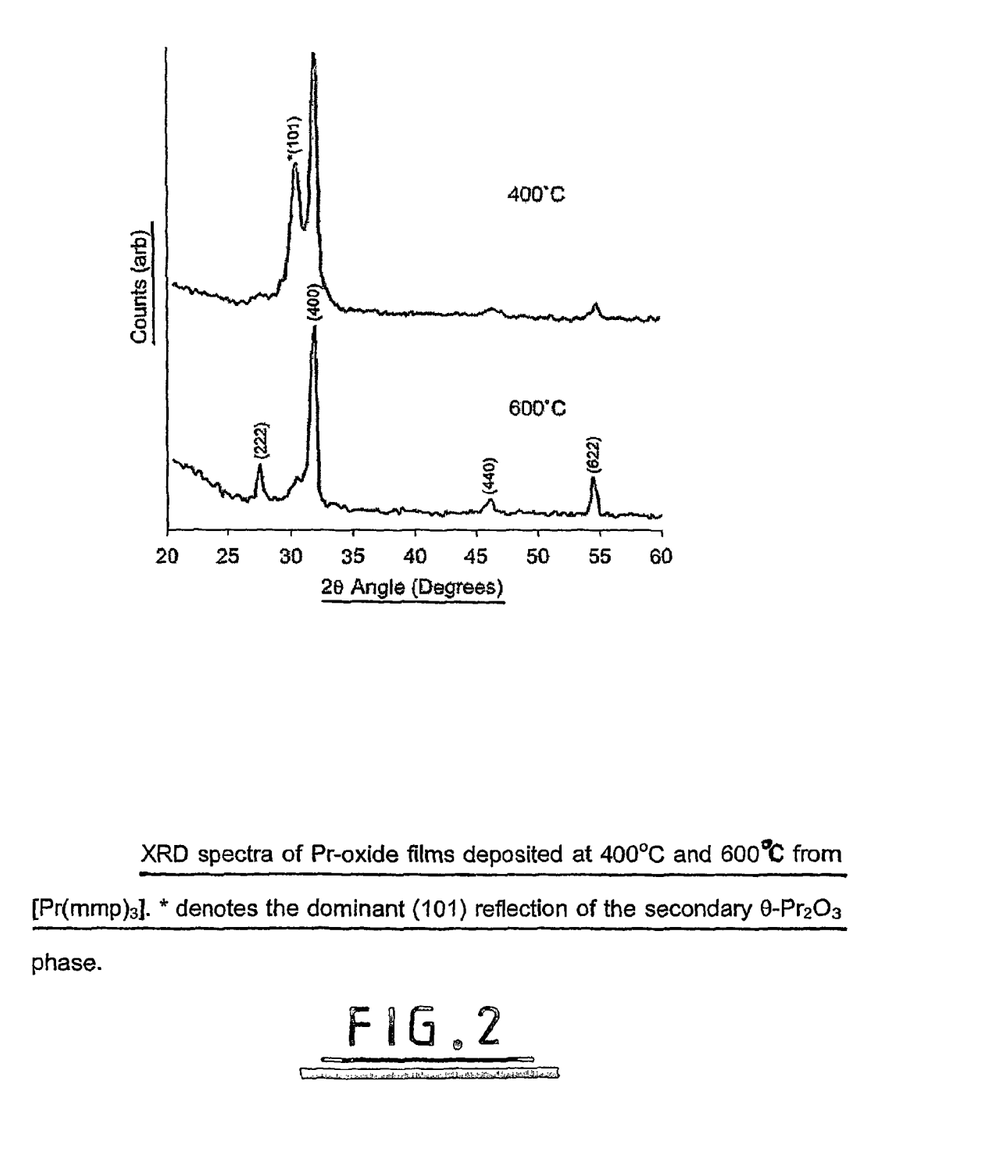
FIG. 2 shows XRD spectra of Pr-oxide films deposited at 400° C. and 600° C. from [Pr(mmp)$_3$]. * denotes the dominant (101) reflection of the secondary θ-Pr$_2$O$_3$ phase.

The identity of the films was confirmed as praseodymium oxide by as X-ray diffraction analysis (see FIG. 2 of the drawings), which indicated that the films comprise a major β-Pr$_6$O$_{11}$ phase with a minor component of the hexagonal θ-Pr$_2$O$_3$ phase. Reports elsewhere (R. Lo Nigro, R. G. Toro, G. Malandrino, V. Raineri, I. L. Fragala, Proceedings of EURO CVD 14, Apr. 27-May 2, 2003, Paris France (eds. M. D. Allendorf, F. Maury, F. Teyssandier), *Electrochem. Soc. Proc.* 2003, 2003-08, 915) indicate that the proportions of the β-Pr$_6$O$_{11}$ phase and the θ-Pr$_2$O$_3$ can be controlled via the partial pressure of oxygen used during MOCVD growth.

Figure 3:
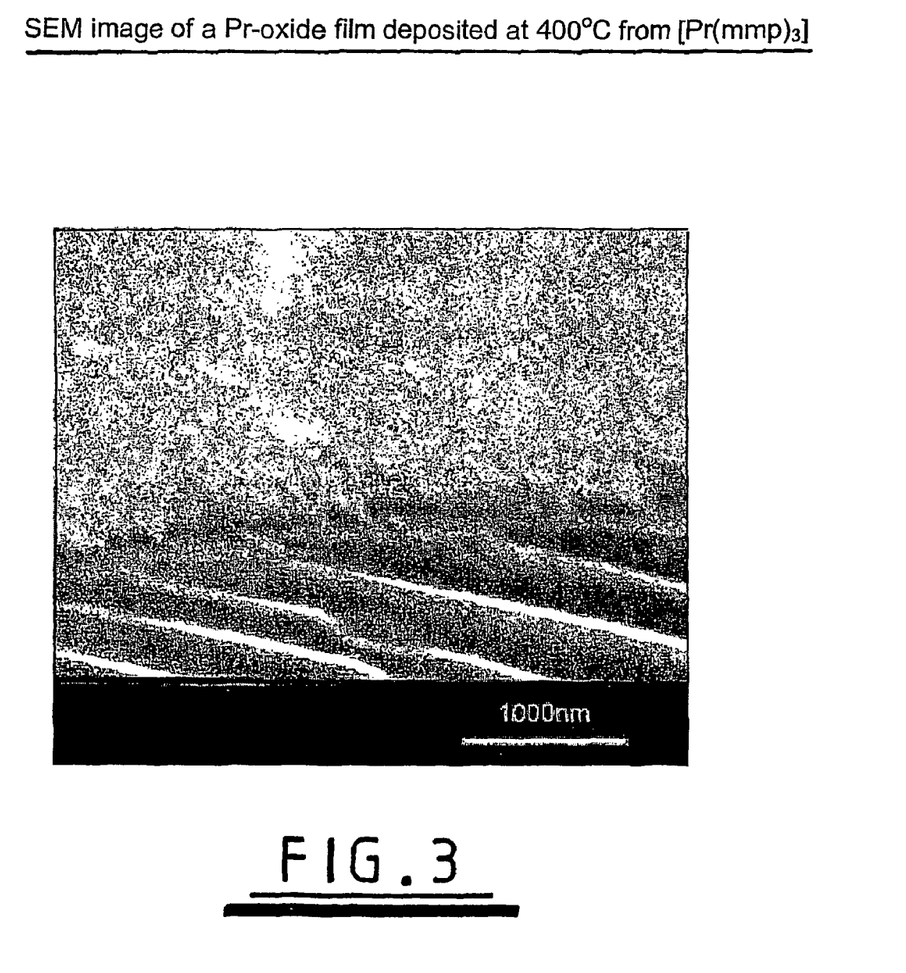
FIG. 3 is an SEM image of a Pr-oxide film deposited at 400° C. from [Pr(mmp)$_3$]

Analysis of the films by scanning electron microscopy (SEM) showed that all the as-grown films exhibited smooth surfaces and uniform cross sectional thicknesses. The cross section of a film grown at 400° C. is shown in FIG. 3 of the drawings and shows no evidence of features such as columnar growth, which has been observed in other high-k dielectric films such as $HfO_2$ and $ZrO_2$.

Point energy dispersive X-ray analyses of the films indicates only Pr from the thin film and silicon from the underlying substrate material.

Further analysis by auger electron spectroscopy (AES) analysis of Pr-oxide films deposited from [Pr(mmp)$_3$] (see Table 2) showed that the films are pure Pr-oxide, with no detectable carbon.

TABLE 2

| Sample | Deposition temperature (° C.) | Pr | Composition O | (at. %) C | Pr/O ratio |
|---|---|---|---|---|---|
| 1 | 350 | 30.3 | 69.7 | ND | 2.3 |
| 4 | 600 | 32.9 | 67.1 | ND | 2.0 |

EXAMPLE 3

Preparation of La(mmp)$_3$

MmpH (3 mol. equiv.) was added to a solution of [La{N(Sime$_3$)$_2$}$_3$] (1 Mol equiv.) in toluene. The solution was stirred at room temperature for 10 min and then solvent and HN(SiMe$_3$)$_2$ was removed in vacuo to give the product.

Microanalysis: Found. C, 40.0; H, 7.4%. Calcd. For $C_{15}H_{33}O_6La$ C, 40.2; H, 7.4%.

IR (ν cm$^{-1}$, neat liquid, NaCl): 2960 vs; 1496 m; 1457 s; 1384 m; 1357 s; 1261 s; 1229 vs; 1172 vs; 1090 vs; 1084 vs; 1001 s; 965 vs; 944 s; 914 m; 841 m; 821 m; 794 s; 730 s; 695 m.

NMR spectroscopy C$_6$D$_6$ (400 MHz) Main resonances: δ (ppm): 3.16 br singlet; 3.08 br singlet (total 5H); 2.65 singlet; 1.27 singlet (6H). Other resonances 3.2-4 ppm, complex pattern (total approx 2H); 1.2-1.8 ppm, complex pattern (total approx 4H).

The same general preparative method can be used for the synthesis of other M(mmp)$_3$ complexes where M=Group IIIB element such as Sc and Y, or a lanthanide (rare earth) element such as, Ce, Gd or Nd.

EXAMPLE 4

La(mmp)$_3$ was found to be a suitable precursor for the deposition of lanthanum oxide thin films by MOCVD. Growth conditions used to deposit La-oxide thin films by liquid injection MOCVD using a toluene solution of La(mmp)$_3$ are summarised in Table 3.

TABLE 3

| | |
|---|---|
| Substrate Temperature | 300-600° C. |
| Evaporator Temperature | 170° C. |
| Pressure | 1 mbar |
| Injection Rate | 8 cm$^3$h$^{-1}$ |
| Solvent | Toluene + 3 mol. eq. tetraglyme |
| Concentration | 0.1 M |
| Argon flow rate | 400 cm$^3$min$^{-1}$ |
| Oxygen flow rate | 100 cm$^3$min$^{-1}$ |
| Run time | 1 h |

Figure 4:
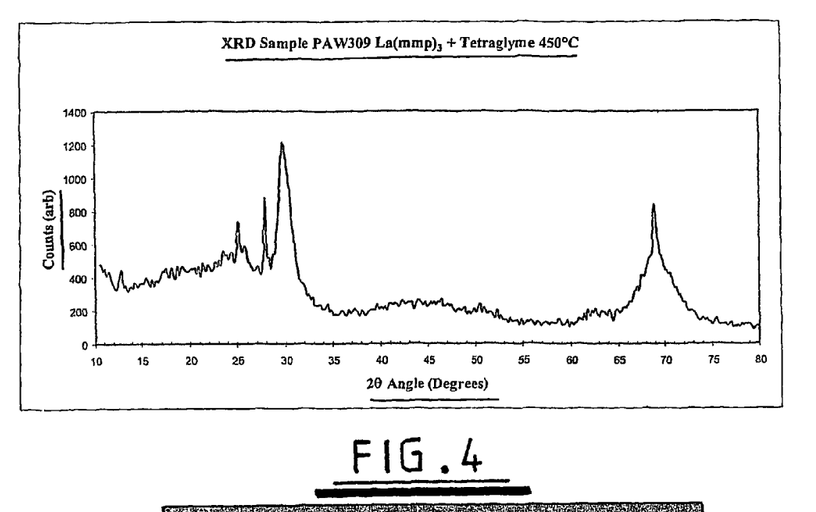
FIG. 4 is an X-ray diffraction pattern of a film of lanthanum oxide deposited at 450° C. from La(mmp)$_3$.

The X-ray diffraction pattern (see FIG. 4 of the drawings) of a film deposited at 450° C. exhibits three dominant diffraction peaks attributed to the (100), (002) and (101) reflections measured at 2θ values of 25.1°, 27.9° and 29.7° respectively. The approximate ratio of intensities of these peaks is consistent with the random powder diffraction pattern of $La_2O_3$ with a hexagonal structure. The width of the observed reflections is notable and consistent with either very small grain size or the transformation of the oxide to the monoclinic LaO(OH) arising from exposure of the film to the ambient environment.

The atomic composition of the LaO$_x$ films was determined using Auger electron spectroscopy (AES), and the results are summarized in Table 4.

TABLE 4

AES analysis of La-oxide films grown by MOCVD

| Film no. | Deposition temperature (° C.) | Argon flow rate (cm$^3$ min$^{-1}$) | Oxygen flow rate (cm$^3$ min$^{-1}$) | Composition La | (atom %) O | O/La |
|---|---|---|---|---|---|---|
| 317 | 300 | 400 | 100 | 29.0 | 71.0 | 2.4 |
| 314 | 350 | 400 | 100 | 35.0 | 65.0 | 1.8 |
| 318 | 400 | 400 | 100 | 33.8 | 66.2 | 1.9 |
| 309 | 450 | 400 | 100 | 31.3 | 68.7 | 2.2 |
| 316 | 500 | 400 | 100 | 33.0 | 67.0 | 2.0 |
| 313 | 550 | 400 | 100 | 33.7 | 66.3 | 2.0 |
| 315 | 600 | 400 | 100 | 31.8 | 68.2 | 2.1 |
| 319 | 450 | 500 | 0 | 34.4 | 65.6 | 1.9 |
| 320 | 450 | 250 | 250 | 32.3 | 67.7 | 2.1 |

The O:La ratios of 1.8-2.4 are consistent with the films being $La_2O_3$ containing excess oxygen (expected O:La ratio in $La_2O_3$=1.5). Carbon was not detected in any of the films at the estimated detection limit of <0.5 at.-% and carbon-free La-oxide films were obtained, even in the absence of oxygen, so that [La(mmp)$_3$] is effectively acting as a "single-source" oxide precursor.

Figure 5:
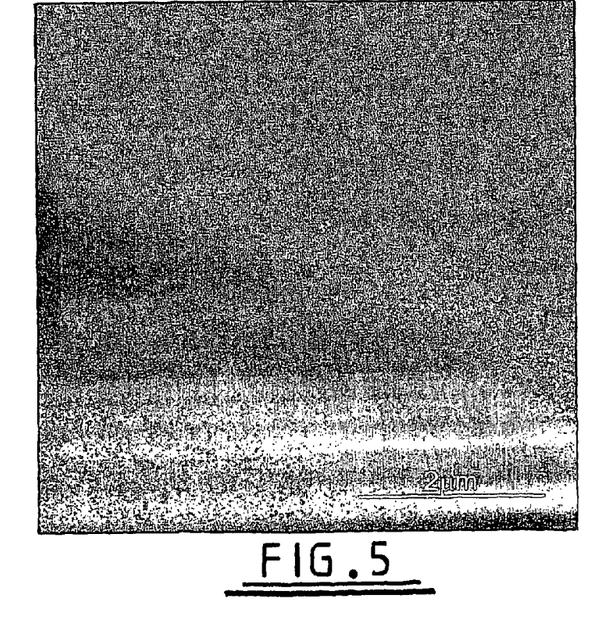
FIG. 5 is a scanning electron micrograph (SEM) of a fracture sample of the lanthanum oxide film of Example 4.

A scanning electron micrograph (SEM) of a fracture sample from that lanthanum oxide film deposited at 450° C. is shown in FIG. 5 of the drawings. A columnar growth habit is discernable which has associated 'hillock' features on the free growth surface causing a fine surface roughening effect.

EXAMPLE 5

Preparation of Nd(mmp)$_3$

Mm pH (3 mol. equiv.) was added to a solution of [Nd{N(SiMe$_3$)$_2$}$_3$] (1 mol.) equiv.) in toluene. The solution was stirred at room temperature for 10 min. and then solvent and HN(SiMe$_3$)$_2$ was removed in vacuo to give the product.

Microanalysis: Found: C, 38.8; H, 6.9%. Calcd. For $C_{15}H_{33}O_6Nd$, C, 39.7; H, 7.33%. Infrared data: recorded as thin film between NaCl plates (cm$^{-1}$)

2963 s; 1496 m; 1457 s; 1384 m; 1357 s; 1275 s; 1231 vs; 1173 vs; 1117 vs; 1086 vs; 1010 s; 968 vs; 915 m; 823 m; 793 a; 730 s; 695 m $^1$H NMR (CDCl$_3$) [resonances are broadened due to paramagnetism of Nd$^{3+}$ (4f$^3$)]: 35.1, 31.7, 30.9, 18.8, 17.4, 15.8, 12.6, 11.5, 8.2, 5.6, 1.2, −9.0, −9.6, −18.2, −24.5, −25.6, −26.0, −55.8, −57.5

EXAMPLE 6

Use of Additives to Stabilise Precursor Solutions

Figure 6:
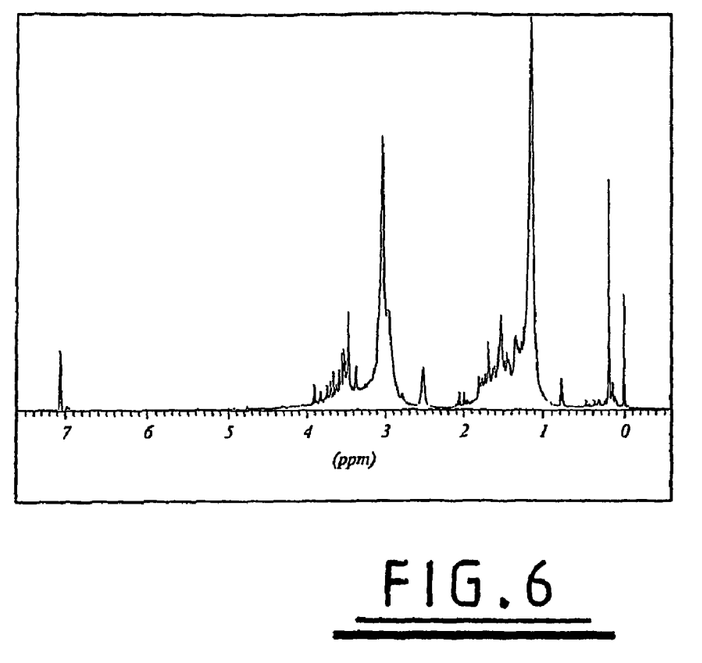
FIG. 6 is a $^1$H NMR spectrum of a solution of La(mmp)$_3$ in toluene.
Figure 7:
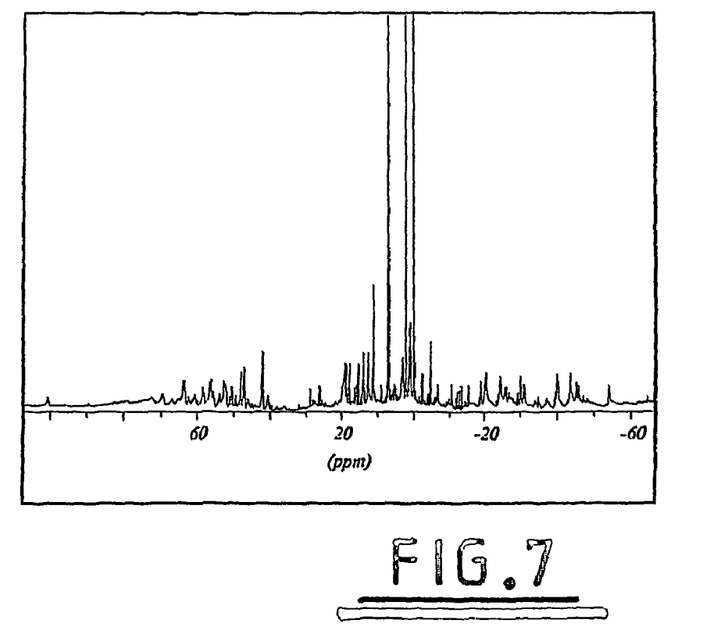
FIG. 7 is a $^1$NMR spectrum of a solution of Pr(Mmp)$_3$ in toluene.

The $^1$H NMR spectra of [La(mmp)$_3$] and [Pr(mmp)$_3$] in toluene solution are shown in FIGS. 6 and 7, respectively. The complexity of the $^1$H NMR data indicates that the structure of both these compounds are extremely complex, and particularly in the case of La, the complexity of the spectrum increases with time. This indicates that there is a significant amount of irreversible molecular aggregation in solution. This process is probably due to condensation reactions to form oxo-bridged oligomers; such reactions are well documented in lanthanide alkoxide chemistry. The resonances are also broadened, possibly due to inter-molecular ligand exchange reactions, commonly observed in solutions of metal alkoxide complexes.

Figure 8:
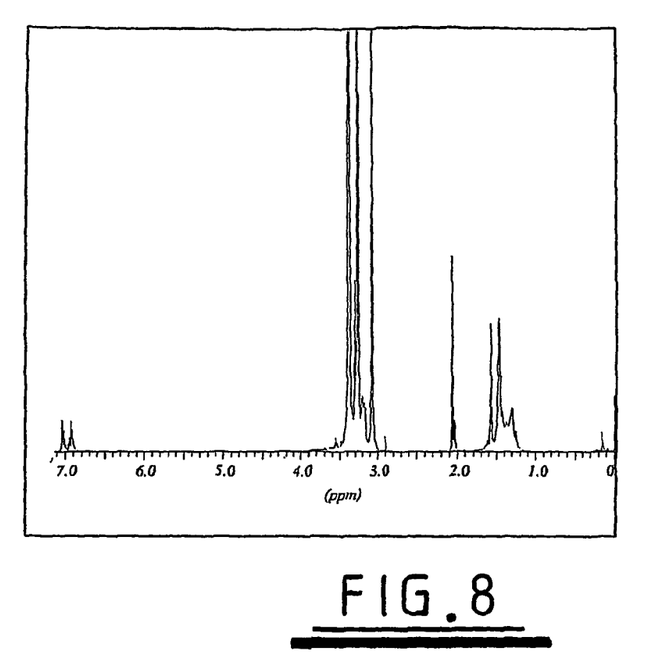
FIG. 8 is a $^1$H NMR spectrum of a solution of La(mmp)$_3$ in toluene with 3 mol. equiv. of added tetraglyme.
Figure 9:
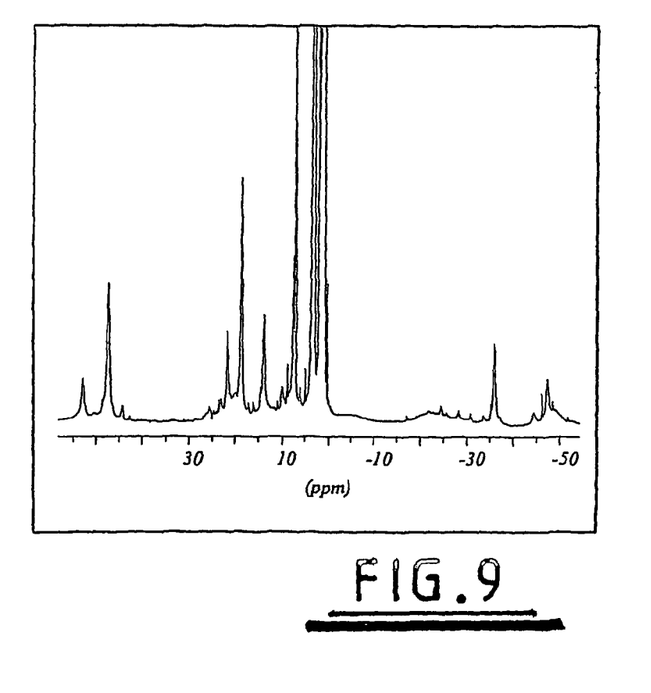
FIG. 9 is a $^1$H NMR spectrum of a solution of Pr(mmp)$_3$ in toluene with 3 mol. equiv. of added tetraglyme.

Significantly, the addition of 3 mol. equivalents of the polydentate oxygen donor ligand tetraglyme, ($CH_3O(CH_2CH_2O)_4CH_3$), to the precursor solutions results in much simpler $^1$H NMR spectra (FIGS. 8 and 9). This strongly suggests that the presence of ($CH_3O(CH_2CH_2O)_4CH_3$) inhibits molecular aggregation. The observation that the tetraglyme resonances are not subject to paramagnetic shifting in [Pr(mmp)$_3$][tetraglyme] indicates that the tetraglyme is not bonded directly to Pr, and we, therefore, conclude that stable adducts of the type [Ln(mmp)$_3$(tetraglyme)] are not formed.

The addition of one mole excess of [mmpH] ($HOCMe_2CH_2OMe$) to toluene solutions of La(mmp$_3$) or Pr(mmp)$_3$ also results in simpler $^1$H NMR spectra (see FIGS. 10 and 11 of the drawings) and has a similar stabilizing effect. The simplicity of the $^1$H NMR spectra indicates that mmp and mmpH are in rapid exchange and there is no uncoordinated mmpH. The addition of tetraglyme or mmpH to solutions of [Ln(mmp)$_3$] was found to enhance air/moisture stability as well as prevent aggregate formation. The mechanism of this stabilization has not been established, but it is likely to be due to some form of shielding of the lanthanide metal centre from oxygen atoms on mmp ligands on neighbouring molecules.

EXAMPLE 7

Preparation of Gd(mmp)$_3$

[Gd(mmp)$_3$] was synthesised by the addition of mmpH (3 mol. equiv.) to a solution of [Gd{N(SiMe$_3$)$_2$}$_3$] (1 mol equiv.) in toluene. The solution was stirred at room temperature for 10 min and then the solvent and liberated HN(SiMe$_3$)$_2$ were removed in vacuo to give the product as a green oil. The product was confirmed by elemental microanalysis for C and H.

EXAMPLE 8

Growth of Gadolinium Oxide using Gd(mmp)$_3$

Gadolinium oxide films were deposited on Si(100) substrates at 1 mbar using a liquid injection MOCVD reactor. The films were deposited over the temperature range 300-600° C. using a 0.1M solution of [Gd(mmp)$_3$] in toluene, with 3 equivalents of added tetraglyme using the same growth conditions to those given in Table 3. Gadolinium oxide films were also grown on GaAs(100) using a 0.1M solution of [Gd (mmp)$_3$] in toluene, with 3 equivalents of added tetraglyme, in the absence of added oxygen.

The films grown on Si(100) and GaAs(100) substrates were confirmed to be Gadolinium oxide by Auger electron spectroscopy (AES) as shown in the following Table 5:—

TABLE 5

Atomic composition (at.-%) of gadolinium oxide films measured by AES*

| Film no. | Substrate | Deposition temp. (° C.) | Argon flow rate (cm$^3$ min$^{-1}$) | Oxygen flow rate (cm$^3$ min$^{-1}$) | Gd | O | O/Gd |
|---|---|---|---|---|---|---|---|
| 1 | Si(100) | 450 | 500 | 0 | 37.6 | 62.4 | 1.7 |
| 2 | GaAs(100) | 450 | 500 | 0 | 36.9 | 63.1 | 1.7 |

*H not analysed for.

X-ray diffraction data for Gd$_2$O$_3$ films showed that at growth temperatures above 450 ÛC, the GdO$_x$ films crystallize as Gd$_2$O$_3$ with a C-type structure exhibiting a preferred (111) orientation. At lower growth temperatures the data exhibited no diffraction features suggesting an amorphous disordered structure.

The diffraction pattern of the Gd$_2$O$_3$ film deposited on GaAs(100) at 450 ÛC was dominated by the (222) reflection. This indicates a strong preferred orientation or a heteroepitaxial relation with the underlying GaAs.

EXAMPLE 9

Stabilisation of M(mmp)$_3$ (M=Rare Earth Element) Precursor Solutions by the Addition of Donor Additives The $^1$H NMR spectra of [La(mmp)$_3$] and [Pr(mmp)$_3$] in toluene solution are shown in FIGS. 6 and 7, respectively. The addition of 3 mole equivalents of the polydentate oxygen donor ligand tetraglyme, ($CH_3O(CH_2CH_2O)_4CH_3$) to the precursor solutions of M(mmp)$_3$ (M=La, Pr) results in much simpler $^1$H NMR spectra (FIGS. 8 and 9 of the drawings) and renders the precursor solutions less air sensitive, and significantly improves the evaporation characteristics of the precursor solution in liquid injection MOCVD applications.

This strongly suggests that the presence of ($CH_3O (CH_2CH_2O)_4CH_3$) inhibits molecular aggregation. The observation that the tetraglyme resonances are not subject to paramagnetic shifting in [Pr(mmp)$_3$][tetraglyme] indicates that the tetraglyme is not bonded directly to Pr, and we, therefore, conclude that stable adducts of the type [Ln(mmp)$_3$(tetraglyme)] are not formed.

Figure 10:
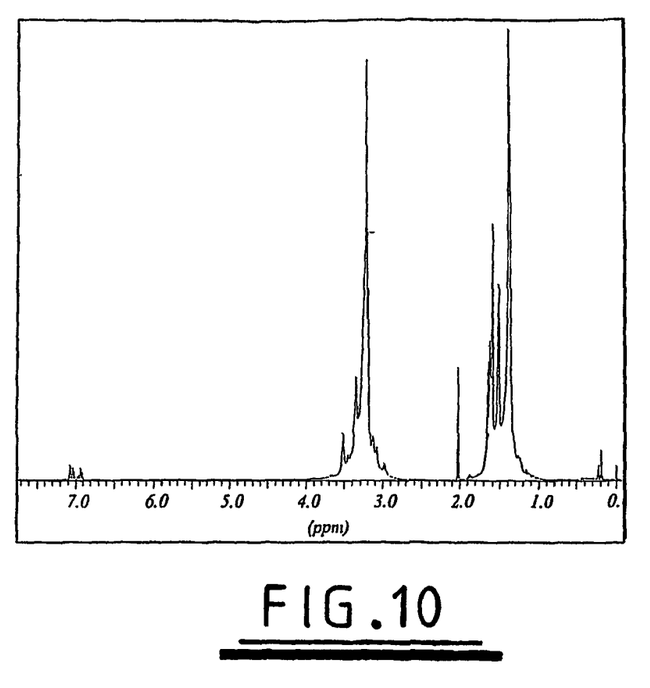
FIG. 10 shows $^1$H NMR data of a solution of La(mmp)$_3$ in toluene with 3 mol. equiv. of added mmpH.
Figure 11:
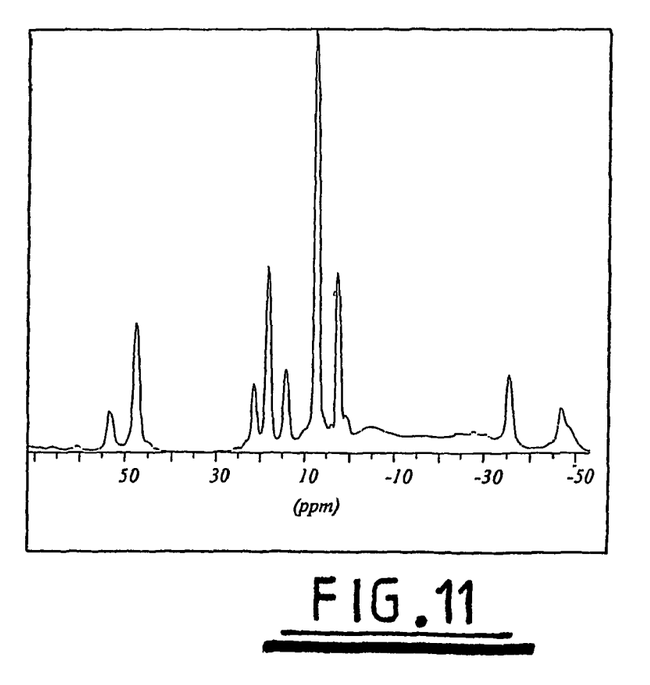
FIG. 11 shows $^1$H NMR data of a solution of Pr(mmp)$_3$ in toluene with 3 mol. equiv. of added mmpH.

The addition of one mole excess of 1-methoxy-2-methyl-2-propanol, [HOCMe$_2$CH$_2$OMe] (mmpH) to solutions of M(mmp)$_3$ (M=rare earth element) in toluene has a similar stabilizing effect (see FIGS. 10 and 11). In the case of [Ln (mmp)$_3$(mmpH)] the simplicity of the $^1$H NMR spectrum indicates that mmp and mmpH are in rapid exchange and there is no uncoordinated mmpH. The addition of tetraglyme or mmpH to solutions of [Ln(mmp)$_3$] was found to enhance air/moisture stability as well as prevent aggregate formation.

The mechanism of this stabilization has not been established, but it is likely to be due to some form of shielding of the Ln metal centre from oxygen atoms on mmp ligands on neighbouring molecules.

EXAMPLE 10

Growth of Neodymium Oxide Using Nd(mmp)$_3$

Neodymium oxide films were deposited on Si(100) substrates at 1 mbar using a liquid injection MOCVD reactor. The films were deposited over the temperature range 250-600° C. using a 0.1M solution of [Nd(mmp)$_3$] in toluene, with 3 equivalents of added tetraglyme employing the equivalent growth conditions to those given in Table 3. Neodymium oxide films were also grown on GaAs(100) using a 0.1 M solution of [Gd(mmp)$_3$] in toluene, with 3 equivalents of added tetraglyme, in the absence of added oxygen.

The films grown on Si(100) and GaAs(100) substrates were confirmed to be neodymium oxide, Nd$_2$O$_3$, by Auger electron spectroscopy (AES) as shown in the following Table 6:—

TABLE 6

Atomic composition (at.-%) of the NdO$_x$ films measured by AES*

| Film no. | Substrate | Deposition temperature (° C.) | Argon flow rate (cm$^3$ min$^{-1}$) | Oxygen flow rate (cm$^3$ min$^{-1}$) | Nd | O | O/Nd |
|---|---|---|---|---|---|---|---|
| 1 | Si(100) | 300 | 400 | 100 | 37 | 63 | 1.7 |
| 2 | Si(100) | 450 | 400 | 100 | 40.1 | 59.9 | 1.5 |
| 3 | Si(100) | 500 | 400 | 100 | 38.7 | 61.3 | 1.6 |
| 4 | Si(100) | 450 | 500 | 0 | 41.2 | 58.8 | 1.4 |
| 5 | Si(100) | 450 | 450 | 50 | 41.8 | 58.2 | 1.4 |
| 6 | Si(100) | 450 | 350 | 150 | 41.7 | 58.3 | 1.4 |
| 7 | Si(100) | 450 | 300 | 200 | 45.5 | 54.5 | 1.2 |
| 8 | Si(100) | 450 | 250 | 250 | 42.1 | 57.9 | 1.4 |
| 9 | GaAs(100) | 450 | 500 | 0 | 40.6 | 59.4 | 1.5 |

*H not analysed for

The invention claimed is:

1. A method of depositing a single or mixed metal oxide layer or film by liquid injection MOCVD, the method comprising using a rare earth metal precursor corresponding in structure to the formula

M[OCR$^1$(R$^2$)(CH$_2$)X]$_3$ wherein M is a rare earth metal, R$^1$ is H or an alkyl group, R$^2$ is an alkyl group optionally substituted with an alkoxy group, X is selected from the group consisting of OR and NR$_2$, wherein R is an alkyl group optionally substituted with an alkoxy group, wherein the rare earth metal precursor is dissolved in an appropriate inert organic solvent containing an additive different from the solvent and selected from the group consisting of one or more polydentate ether and donor functionalized alcohol.

2. The method as claimed in claim 1, wherein the inert organic solvent comprises a solvent selected from the group consisting of an aliphatic hydrocarbon, an aromatic hydrocarbon, an aliphatic ether, and a cyclic ether.

3. The method as claimed in claim 2, wherein the inert organic solvent comprises an aliphatic hydrocarbon solvent selected from the group consisting of hexane, heptane and nonane.

4. The method as claimed in claim 2, wherein the aromatic hydrocarbon solvent is toluene.

5. The method as claimed in claim 1, wherein the polydentate ether is selected from the group consisting of CH$_3$O(CH$_2$CH$_2$O)$_2$CH$_3$, CH$_3$O(CH$_2$CH$_2$O)$_3$CH$_3$, and CH$_3$O(CH$_2$CH$_2$O)$_4$CH$_3$.

6. The method as claimed in claim 1, wherein the additive is 1-methoxy-2-methyl-2-propanol.

7. The method as claimed in claim 1, wherein the amount of additive in the solvent is at least 3 mol. equiv.: 1 mol. equiv. of precursor.

8. The method as claimed in claim 7, wherein the amount of additive in the solvent is about 3 mol. equiv.

9. The method as claimed in claim 1, wherein M is praseodymium or lanthanum.

10. The method as claimed in claim 1, wherein [OCR$^1$(R$^2$)(CH$_2$)X] is [OCMe$_2$CH$_2$OMe].

11. The method as claimed in claim 1, wherein [OCR$^1$(R$^2$)(CH$_2$)X] is selected from the group consisting of
OCH(Me)CH$_2$OMe, OCEt$_2$CH$_2$OMe, OCH(Et)CH$_2$OMe, OC(Pr$^i$)$_2$CH$_2$OMe, OCH(Pr$^i$)CH$_2$OMe, OC(Bu$^t$)$_2$CH$_2$OMe, OCH(Bu$^t$)CH$_2$OMe,
OCH(Bu$^t$)CH$_2$OEt, OC(Bu$^t$)$_2$CH$_2$OEt, OC(Pr$^i$)$_2$CH$_2$OEt and OCH(Bu$^t$)CH$_2$NEt$_2$.

12. The method as claimed in claim 1, wherein the precursor is Pr(OCMe$_2$CH$_2$OMe)$_3$.

13. The method as claimed in claim 1, wherein the precursor is La(OCMe$_2$CH$_2$OME)$_3$.

14. The method as claimed in claim 1, wherein the precursor is Gd(OCMe$_2$CH$_2$OMe)$_3$.

15. The method as claimed in claim 1, wherein the precursor is Nd(OCMe$_2$CH$_2$OMe)$_3$.

16. The method as claimed in claim 1, wherein M is selected from the group consisting of La, Ce, Gd, Nd, Pm, Sm, Eu, Tb, Dy, Ho, Er, Tm, Yb, Lu, and Group IIIB elements.

17. The method as claimed in claim 1, carried out with an appropriate co-precursor, for the MOCVD of a mixed metal oxide layer or film.

18. A method of depositing a single or mixed metal oxide layer or film by atomic layer deposition, the method comprising using a rare earth metal precursor corresponding in structure to

M[OCR$^1$(R$^2$)CH$_2$X]$_3$, wherein M is a rare earth metal, R$^1$ is H or an alkyl group, R$^2$ is an alkyl group optionally substituted with an alkoxy group, X is selected from the group consisting of OR and NR$_2$, wherein R is an alkyl group optionally substituted with an alkoxy group.

19. The method as claimed in claim 18, wherein M is praseodymium or lanthanum.

20. A method of depositing a single or mixed metal oxide layer or film by a non-vapor phase deposition technique, the method comprising using a rare earth metal precursor corresponding in structure to

M[OCR$^1$(R$^2$)CH$_2$X]$_3$, wherein M is a rare earth metal, $R^1$ is H or an alkyl group, $R^2$ is an alkyl group optionally substituted with an alkoxy group, X is selected from the group consisting of OR and $NR_2$, wherein R is an alkyl group optionally substituted with an alkoxy group.

21. The method as claimed in claim 20, wherein the non-vapor technique is selected from the group consisting of sol-gel deposition and metal-organic decomposition.

* * * * *

UNITED STATES PATENT AND TRADEMARK OFFICE
CERTIFICATE OF CORRECTION

PATENT NO. : 7,927,661 B2
APPLICATION NO. : 10/548946
DATED : April 19, 2011
INVENTOR(S) : Anthony Copeland Jones It is certified that error appears in the above-identified patent and that said Letters Patent is hereby corrected as shown below:

(1) replace "allcoxides" with --alkoxides-- at column 1, line 63;

(2) replace "Pr{N(Sie$_3$)$_2$}$_3$" with --Pr{N(SiMe$_3$)$_2$}$_3$-- at column 2, line 45;

(3) replace "Th" with --Tb-- at column 3, line 25;

(4) replace "are note reported" with --are not reported-- at column 4, line 12; and (5) replace "[La{N(Sime$_3$)$_2$}$_3$]" with --[La{N(SiMe$_3$)$_2$}$_3$]-- at column 5, line 25-26

Signed and Sealed this
Ninth Day of August, 2011

David J. Kappos
*Director of the United States Patent and Trademark Office*